(12) United States Patent
Longo et al.

(10) Patent No.: US 12,185,747 B2
(45) Date of Patent: Jan. 7, 2025

(54) FASTING-MIMICKING DIET (FMD) AS AN INTERVENTION FOR ALZHEIMER'S DISEASE (AD)

(71) Applicant: UNIVERSITY OF SOUTHERN CALIFORNIA, Los Angeles, CA (US)

(72) Inventors: Valter D. Longo, Playa del Rey, CA (US); Min Wei, West Covina, CA (US); Priya Rangan, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 925 days.

(21) Appl. No.: 16/863,418

(22) Filed: Apr. 30, 2020

(65) Prior Publication Data

US 2020/0345053 A1    Nov. 5, 2020

Related U.S. Application Data

(60) Provisional application No. 62/840,762, filed on Apr. 30, 2019.

(51) Int. Cl.

| | |
|---|---|
| *A23L 33/20* | (2016.01) |
| *A23L 33/00* | (2016.01) |
| *A61K 9/00* | (2006.01) |
| *A61K 47/26* | (2006.01) |
| *A61K 47/42* | (2017.01) |
| *A61K 47/44* | (2017.01) |

(52) U.S. Cl.
CPC .............. *A23L 33/20* (2016.08); *A23L 33/30* (2016.08); *A23L 33/40* (2016.08); *A61K 9/0053* (2013.01); *A61K 47/26* (2013.01); *A61K 47/42* (2013.01); *A61K 47/44* (2013.01)

(58) Field of Classification Search
CPC ......... A61K 47/26; A61K 47/42; A61K 47/44
USPC ........................................................ 426/648
See application file for complete search history.

(56) References Cited

U.S. PATENT DOCUMENTS

| | | |
|---|---|---|
| 8,211,700 B2 | 7/2012 | Longo |
| 8,728,815 B2 | 5/2014 | Longo |
| 8,865,646 B2 | 10/2014 | Longo |
| 9,237,761 B2 | 1/2016 | Longo et al. |
| 9,386,790 B2 | 7/2016 | Longo et al. |

(Continued)

FOREIGN PATENT DOCUMENTS

| | | |
|---|---|---|
| KR | 20080079707 | 9/2008 |
| WO | 2011/050302 A2 | 4/2011 |

(Continued)

OTHER PUBLICATIONS

Medical Articles by Dr Ray, Fast Mimicking Diet, Dec. 30, 2017, accessed at https://www.askdrray.com/fasting-mimicking-diet/.*
Bloom, G.S., "Amyloid-β and Tau The Trigger and Bullet in Alzheimer Disease Pathogenesis," JAMA Neurology, v. 71, n. 4, 2014, pp. 505-508.

(Continued)

*Primary Examiner* — Donald R Spamer
*Assistant Examiner* — Philip A Dubois
(74) *Attorney, Agent, or Firm* — Brooks Kushman P.C.

(57) ABSTRACT

A method of treating Alzheimer's associated pathology includes a step of identifying subject having a pathology that is associated with Alzheimer's disease. A fasting mimicking diet (FMD) is then administered to the subject for a first time period. Methods for treating amyloid plaque formation and/or elevated levels of tau protein as well as neuroinflammation are also provided.

15 Claims, 12 Drawing Sheets

(56) References Cited

U.S. PATENT DOCUMENTS

| | | |
|---|---|---|
| 10,015,980 B2 | 7/2018 | Longo et al. |
| 10,172,839 B2 | 1/2019 | Longo et al. |
| 10,433,576 B2 | 10/2019 | Longo et al. |
| 2011/0118528 A1 | 5/2011 | Longo et al. |
| 2014/0227373 A1 | 8/2014 | Longo et al. |
| 2014/0328863 A1 | 11/2014 | Longo |
| 2015/0133370 A1 | 5/2015 | Longo |
| 2016/0303056 A1 | 10/2016 | Longo et al. |
| 2016/0306920 A1 | 10/2016 | Soon-Shiong |
| 2016/0324193 A1 | 11/2016 | Longo et al. |
| 2016/0331016 A1 | 11/2016 | Longo et al. |
| 2017/0027217 A1 | 2/2017 | Longo et al. |
| 2017/0035093 A1 | 2/2017 | Longo et al. |
| 2017/0035094 A1 | 2/2017 | Longo et al. |
| 2017/0232053 A1 | 2/2017 | Longo et al. |
| 2017/0185727 A1 | 6/2017 | Harris et al. |
| 2017/0325493 A1 | 11/2017 | Longo et al. |
| 2018/0228198 A1 | 8/2018 | Brandhorst et al. |
| 2018/0301220 A1 | 10/2018 | Rothman |
| 2019/0029301 A1 | 1/2019 | Longo et al. |
| 2020/0029614 A1 | 1/2020 | Longo et al. |

FOREIGN PATENT DOCUMENTS

| | | | |
|---|---|---|---|
| WO | 2016/179466 A1 | 11/2016 | |
| WO | 2018138090 | * 8/2018 | ............. A23L 33/00 |

OTHER PUBLICATIONS

Brandhorst, S. et al., "A Periodic Diet that Mimics Fasting Promotes Multi-System Regeneration, Enhanced Cognitive Performance, and Healthspan," Cell Metabolism 22, 2015, pp. 86-99.

Elder, G.A. et al., "Transgenic Mouse Models of Alzheimer's Disease," Mt. Sinai J. Med., 77(1), 2010, pp. 69-81.

Liu, C-C et al., "Apolipoprotein E and Alzheimer disease: risk, mechanisms, and therapy," Nat Rev Neurol. 2013; 9(2), pp. 106-118.

Parrella, E. et al., "Protein restriction cycles reduce IGF-1 and phosphorylated Tau, and improve behavioral performance in an Alzheimer's disease mouse model," Aging Cell (2013), 12, pp. 257-268.

Wei, M. et al., "Fasting-mimicking diet and markers/risk factors for aging, diabetes, cancer, and cardiovascular disease," Sci Transl Med 2017; 9(377), pp. 1-25.

Youmans, K.L. et al., "APOE4-specific Changes in Aβ Accumulation in a New Transgenic Mouse Model of Alzheimer Disease," The J. of Biological Chemistry, v. 287, n. 50, 2012, pp. 41774-41786.

Wei, M. et al., "Fasting-Mimicking diet and markers/risk factors for aging, diabetes, cancer, and cardiovascular disease," Sci. Transl. Med. 9, Feb. 15, 2017, 12 pgs.

International Search Report dated Aug. 21, 2020 for PCT Appn. No. PCT/US2020/030793 filed Apr. 30, 2020, 3 pgs.

Search Report & Written Opinion dated Dec. 21, 2022 for European Appn. No. 20798070.7, 7 pgs.

* cited by examiner

FASTING-MIMICKING DIET (FMD) AS AN INTERVENTION FOR ALZHEIMER'S DISEASE (AD)

CROSS-REFERENCE TO RELATED APPLICATIONS

This application claims the benefit of U.S. provisional application Ser. No. 62/840,762 filed Apr. 30, 2019, the disclosure of which is hereby incorporated in its entirety by reference herein.

STATEMENT REGARDING FEDERALLY SPONSORED RESEARCH OR DEVELOPMENT

This invention was made with government support under AG055369 awarded by the National Institutes of Health. The government has certain rights in the invention.

TECHNICAL FIELD

In at least one aspect, methods for reducing Alzheimer's-associated pathology and promoting improvement in cognitive performance is provided.

BACKGROUND

Alzheimer's disease (AD) is molecularly characterized as a disorder of excess amyloid beta (Aβ) and tau protein production, with accumulation most prominent in the frontal cortex and hippocampus[1]. Transgenic mouse models have long been used to study AD, and while they do not truly mimic the human condition, they have been useful for understanding the progression and pathogenicity of AB and hyperphosphorylated tau[2]. The positive effects of fasting-mimicking diet (FMD) have been previously demonstrated in aged wild-type mice, as evidenced by improved cognition (FIG. 1), and an increase in adult neurogenesis.[3] In mice and humans, FMD also causes a reduction in biomarkers associated with diabetes, cardiovascular disease, and high blood pressure[3,4], disease conditions that increase the risk of developing AD (alz.org). We have previously shown that an FMD consisting of protein restriction cycles (PRC) can delay cognitive decline and the progression of tau pathology in the 3×Tg-AD mouse model of familial Alzheimer's disease[5].

There are no existing dietary interventions designed with the intention of reducing AD-associated pathology. As for Alzheimer's disease (AD), there are two types of FDA approved medications (i.e., cholinesterase inhibitors and memantine). Cholinesterase inhibitors, including donepezil, galantamine, and rivastigmine, slow down the process that breaks down a key neurotransmitter. Memantine regulates the activity of glutamate, an important neurotransmitter in the brain involved in learning and memory. (http://www.alz.org/research/science/alzheimers_disease_treatments.asp#how). While these drugs treat the symptoms, they do not treat the underlying disease. In addition, these drugs are only accessible to the patients and are not preventative medicine.

Accordingly, there is a need for improved methods for treating pathologies that are associated with Alzheimer's disease.

SUMMARY

In at least one aspect, cycles of a newly developed fasting-mimicking diet (FMD) serve as an intensive but brief form of nutrient restriction that can have a beneficial effect on AD-associated pathology as indicated by reductions in amyloid load and hyperphosphorylated tau levels in the hippocampus as well as improvement of cognitive functions.

In another aspect, a method of treating Alzheimer's associated pathology is provided. The method includes a step of identifying a subject having a pathology that is associated with Alzheimer's disease. A fasting-mimicking diet (FMD) is administered to the subject for a first time period.

In another aspect, a method for treating amyloid plaque formation and/or elevated levels of tau protein is provided. The method includes a step of identifying a subject having amyloid plaque formation and/or elevated levels of tau protein. A fasting-mimicking diet is administered to the subject for a first time period. Typically, the step of administering the fasting-mimicking diet is repeated a plurality of times at predetermined intervals.

In another aspect, a method of treating neuroinflammation is provided. The method includes a step of identifying a subject having neuroinflammation. A fasting-mimicking diet is administered to the subject for a first time period. Typically, the step of administering the fasting-mimicking diet is repeated a plurality of times at predetermined intervals.

In another aspect, a method of treating Mild Cognitive Impairment (MCI) is provided. The method includes a step of identifying a subject having MCI. A fasting-mimicking diet is administered to the subject for a first time period. Typically, the step of administering the fasting-mimicking diet is repeated a plurality of times at predetermined intervals.

Figure 5:
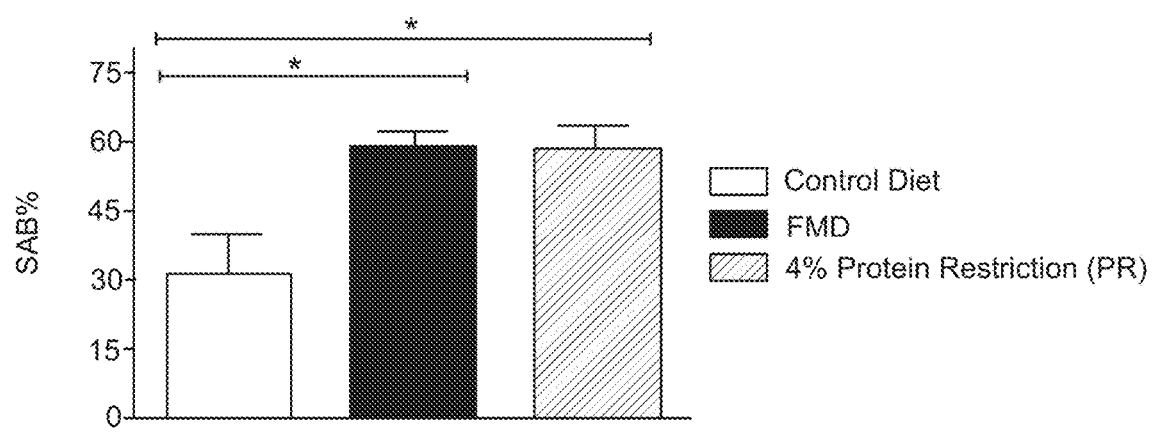

FIG. 5: Bi-weekly FMD cycles improve hippocampal-dependent working short-term memory in 3×Tg-AD mice. Spontaneous alternation behavior (SAB) at the midpoint of study (10.5 months) for female 3×Tg-AD mice. n=9-14/group.

Figure 6A:
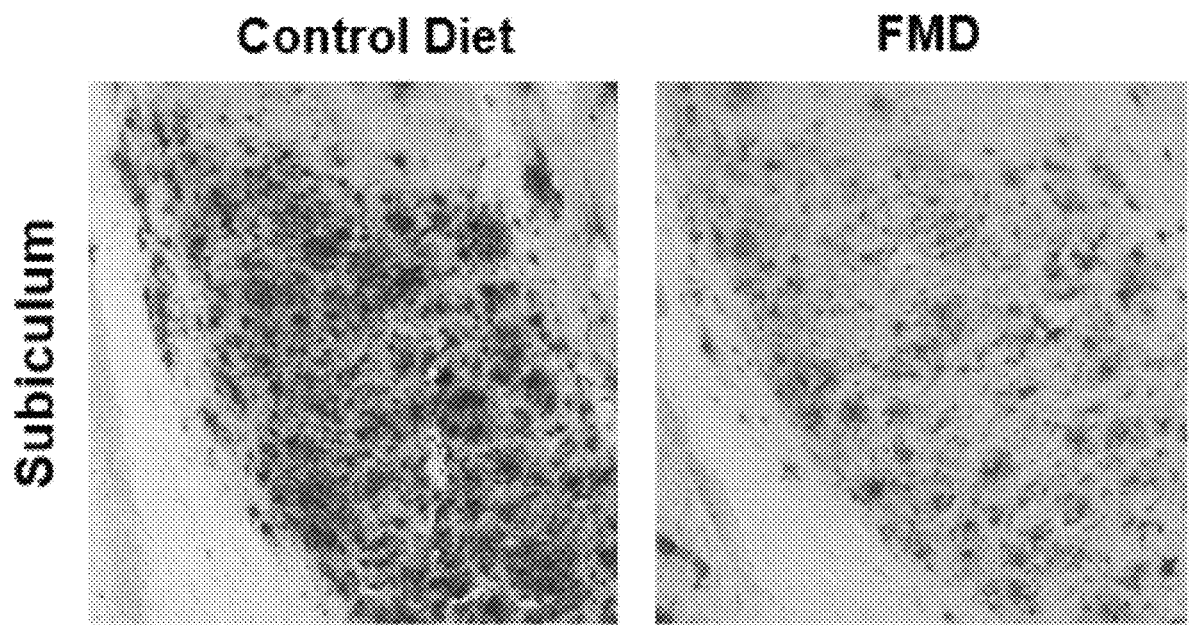
Figure 6B:
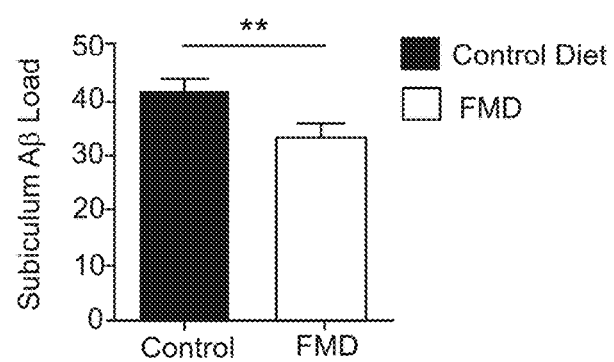

FIGS. 6A and 6B: FMD cycles reduce Aβ plaques in E4FAD female mice. (A) DAB-immunohistochemistry of Aβ plaques in subiculum of 7.5-month-old E4FAD female mice on a control diet or after ~4 months of bi-weekly FMD cycles. (B) Subiculum Aβ load (%) in subiculum CA1 of 7.5-month-old E4FAD female mice on the control diet or after ~4 months of bi-weekly FMD cycles. (n=18/group).

Figure 7A:
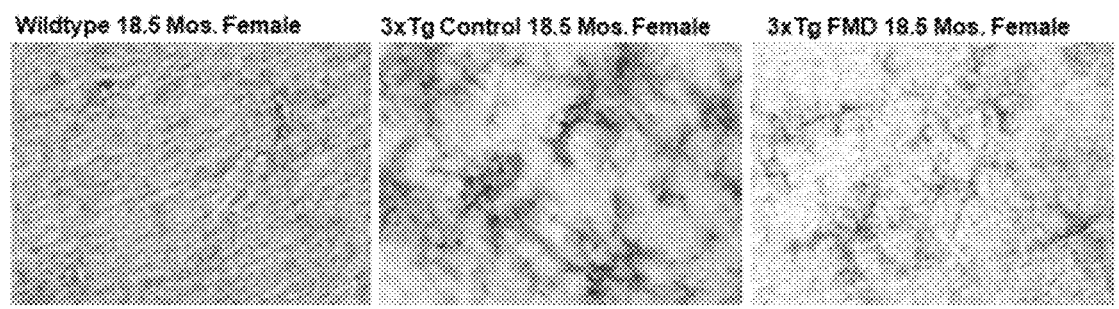
Figure 7B:
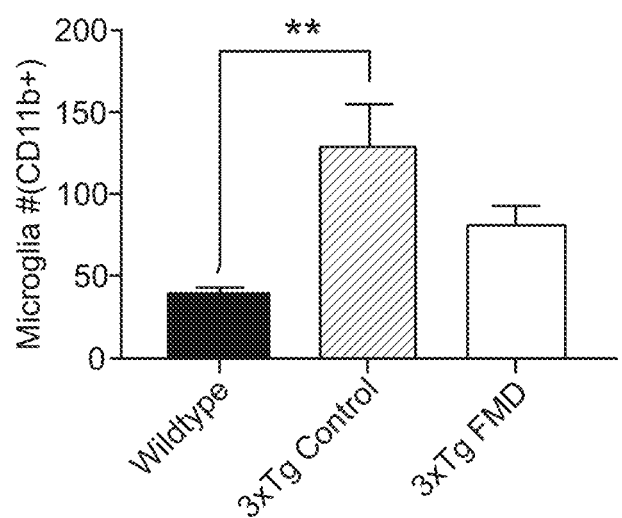

FIGS. 7A and 7B: Bi-weekly FMD cycles mediate neuroinflammation via microglia number in aged 3×Tg mice. (A) Representative images showing CD11b-ir microglia in hippocampus sections of 18.5-month-old female C57B/6 wildtype, 3×Tg Control and 3×Tg FMD mice (top). (B) Quantification of total numbers of CD11b-ir cells in hippocampus CA1 and subiculum combined brain regions of C57B/6 wildtype, 3×Tg Control, and 3×Tg FMD groups (bottom left; n=5-7 animals/group).

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . . 97, 98, 99, 100.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

As used herein, the term "and/or" means that either all or only one of the elements of said group may be present. For example, "A and/or B" shall mean "only A, or only B, or both A and B". In the case of "only A", the term also covers the possibility that B is absent, i.e. "only A, but not B".

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, diet compositions, diet ingredients, and any experimental conditions can be practiced with plus or minus 50 percent of the values indicated rounded to three significant figures. In a refinement diet compositions, diet ingredients, and any experimental conditions can be practiced with plus or minus 30 percent of the values indicated rounded to three significant figures of the value provided in the examples. In another diet compositions, diet ingredients, and any experimental conditions can be practiced with plus or minus 10 percent of the values indicated rounded to three significant figures of the value provided in the examples.

In the examples set forth herein, the diet compositions, diet ingredients, and any experimental conditions can be practiced with plus or minus 50 percent of the values indicated rounded to or truncated to two significant figures of the value provided in the examples. In a refinement, the diet compositions, ingredients, and any experimental conditions can be practiced with plus or minus 30 percent of the values indicated rounded to or truncated to two significant figures of the value provided in the examples. In another refinement, the diet compositions, ingredients, and any experimental conditions can be practiced with plus or minus 10 percent of the values indicated rounded to or truncated to two significant figures of the value provided in the examples.

The term "one or more" means "at least one" and the term "at least one" means "one or more." The terms "one or more" and "at least one" include "plurality" as a subset.

In a refinement, the terms "less than" or "less than or equal to" a given quantity include as an example of a lower limit a value that is 1 percent of the given quantity truncated to 2 significant figures. For example, the phrase "less than 28 grams" includes the range 0.28 grams to 28 grams.

In a refinement, the terms "greater than" or "greater than or equal to" a given quantity include as an example of an upper limit a value that ten times the given quantity truncated to 2 significant figures. For example, the phrase "greater than 28 grams" includes the range 28 grams to 280 grams.

When a subject is characterized as "having" a medical condition or property, "having" means the subject is diagnosed with the medical condition or medical property.

Throughout this application, where publications are referenced, the disclosures of these publications in their entireties are hereby incorporated by reference into this application to more fully describe the state of the art to which this invention pertains.

Abbreviations:

"Aβ" means amyloid beta.
"CTRL" means control.
"FMD" means fasting mimicking diet.
"PET" means positron emission tomography.
"PR" means protein restriction.
"RF" means refeeding.
"WT" means wildtype.

The term "subject" refers to a human or animal, including all mammals such as primates (particularly higher primates), sheep, dog, rodents (e.g., mouse or rat), guinea pig, goat, pig, cat, rabbit, and cow.

The term "fasting mimicking diet" (FMD) means a diet that mimics the effects of fasting typically by providing a subject with at most 50% of their normal caloric intake but with some nutritional component so that fasting is mimicked while a subject is not completely starved. Sometimes the fasting mimicking diet is referred to as a "fasting mimicking and enhancing diets." Examples of useful fasting mimicking and enhancing diets and method for monitoring the effects of these diets on markers such as IGF-1 and IGFBP1 in the context of the present invention are set forth in U.S. patent application Ser. No. 14/273,946 filed May 9, 2014; Ser. No. 14/497,752 filed Sep. 26, 2014; Ser. No. 12/910,508 filed Oct. 22, 2010; Ser. No. 13/643,673 filed Oct. 26, 2012; Ser. No. 13/982,307 filed Jul. 29, 2013; Ser. No. 14/060,494 filed Oct. 22, 2013; Ser. No. 14/178,953 filed Feb. 12, 2014; Ser. No. 14/320,996 filed Jul. 1, 2014; Ser. No. 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful FMD in the present invention. Additional examples of FMD diets are found in U.S. patent application Ser. No. 15/148,251 and WIPO Pub. No. WO2011/050302 and WIPO Pub. No. WO2011/050302; the entire disclosures of which are hereby incorporated by reference. The PROLON® Fasting Mimicking Diet commercially available from L-Nutra, Inc. located in Beverly Hills, California is another example of a fasting mimicking diet useful in the methods and diet package of the present invention. The PROLON® Fasting Mimicking Diet is a high-fat, low-calorie intermittent fasting diet that may promote fat loss and reduce blood sugar, inflammation, and cholesterol. A particularly useful fasting mimicking diet protocol and diet package is found in U.S. Pat. Pub. No. 20180228198; the entire disclosure of which is hereby incorporated by reference in its entirety.

A particularly useful diet for treating Alzheimer's Disease (and the other medical conditions set forth herein provides about 43-47% carbohydrate calories, about 44-46% fat calories and about 9-11% protein calories per day in the form of vegetable soups, broths, bars, olives, crackers, herbal teas. The addition of specific supplements (e.g., olive oil, coconut oil, algal oil, nuts, caffeine and cocoa) that substantially increase the daily calories (e.g., by 300-500 kcal) compared to other FMDs. This diet can have added neuroprotective, anti-inflammatory and antioxidant properties.

The present invention solves one or more problems of the prior art by providing in at least on embodiment, a method for treating pathologies that are typically associated with Alzheimer's disease. The method includes a step of identifying a subject having a pathology associated with Alzheimer's disease. Examples of such pathologies involve the formation of amyloid plaques (e.g., Aβ plaques), and the presence of Tau protein (e.g., in blood or brain tissue). (Johnson K A, Minoshima S, Bohnen N I, et al. Appropriate use criteria for amyloid PET: A report of the Amyloid Imaging Task Force, the Society of Nuclear Medicine and Molecular Imaging, and the Alzheimer's Association. Alzheimer's & Dementia 2013; 9:e1-e16. Grundman M, Johnson K A, Lu M, et al. Effect of Amyloid Imaging on the Diagnosis and Management of Patients with Cognitive Decline: Impact of Appropriate Use Criteria. Dement Geriatr Cogn Disord. 2016; 41(1-2):80-92. doi: 10.1159/000441139. Epub 2016 Jan. 8). It should be appreciated, that the methods set forth herein can be sued to treat these pathologies whether or not the subject has Alzheimer's disease if these pathologies are identified. The presence of amyloid plaques can be measured by amyloid PET scans. Tau proteins can be measured via antibody assay for Tau protein or fragments thereof. An antibody assay for Tau-A and Tau-C fragments has been developed. (Two novel blood-based biomarker candidates measuring degradation of tau are associated with dementia: A prospective study; J. S. Neergaard et al. Apr. 11, 2018; https://doi.org/10.1371/journal.pone.0194802). With or without a diagnosis of Alzheimer's, a patient with visualized amyloid plague formation of elevated levels of tau protein can benefit from the FMD protocol set forth herein. Advantageously, administration of the FMD protocol can delay the onset of overt Alzheimer's disease.

A fasting mimicking diet (FMD) is administered to the subject for a first time period. Typically, the administration of the FMD is repeated a plurality of times at predetermined intervals. In a refinement, the FMD is repeated at intervals from one week to 6 months. In some variations, a normal diet is administered between cycles of the FMD. In this context, a normal diet is a diet of sufficient caloric intake to maintain the subject's weight. In a refinement, the normal caloric intake provides the subject with 1500 to 2500 kcal or 1800 to 2300 kcal, or 1800 to 2000 kcal.

The FMD is administered to the subject for a first time period. In some variations, the first time period is equal to or greater than, in increasing order of preference, 3, 5, 6, or 7 days. In addition, the first time period is equal to or less than, in increasing order of preference, 20, 15, 10, or 8 days. In a refinement, the first time period is 1, 2, 3, 4, 5, 6, 7, 8, 9, or 10 days. In another refinement, the first time period is 3 to 10 days. In another refinement, the first time period is 4 to 8 days. In some variations of the methods set forth herein, the fasting mimicking and enhancing diet is repeated at first intervals. In a refinement, the FMD is administered every 2-12 weeks. For example, the fasting mimicking and enhancing diet can be initiated once a month for the duration of the subject's treatment which can be 3 months to a year or more (e.g., 1 to 5 years).

In some variations, the fasting mimicking diet for each of the methods set forth herein provides at most, in increasing order of preference, 50%, 40%, 30%, or 100% of the subject's normal caloric intake. In a refinement, the fasting mimicking diet provides at least, in increasing order of preference, 5%, 10%, or 20% of the subject's normal caloric intake. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the fasting mimicking diet provides the subject with from 700 to 1200 kcal/day. In a particularly useful refinement, the fasting mimicking diet provides a male subject of average weight with at most 1100 kcal/day and a female subject of average weight with at most 900 kcal/day. In some refinements, the fasting mimicking diet provides at most, in increasing order of preference, 1500 kcal/day, 1400 kcal/day, 1300 kcal/day, 1200 kcal/day, 1100 kcal/day, 1000 kcal/day, 900 kcal/day, 800 kcal/day, 700 kcal/day, 600 kcal/day, 500 kcal/day, or 2500 kcal/day. In some further refinements, the fasting mimicking diet provides at least, in increasing order of preference, 0 kcal/day, 10 kcal/day, 100 kcal/day, 200 kcal/day, 300 kcal/day, 400 kcal/day, or 500 kcal/day.

In certain variations, the fasting mimicking and enhancing diet provides from 4.5 to 7 kilocalories per pound of subject for a first day (day 1) and then 3 to 5 kilocalories per pound of subject per day for the second day to the final day of the fasting mimicking diet. After a cycle of the fasting mimicking and enhancing diet, a second diet is administered to the subject for a second time period. In a refinement, the second diet provides an overall calorie consumption that is within 20 percent of a subject's normal calorie consumption for a second time period of 10 to 26 days (e.g., immediately) following the fasting mimicking and enhancing diet.

The consumption guidelines for the FMD include Nutrition Facts relative to calories, macronutrients and micronutrients. Calories are consumed according to the user's body weight. Total calorie consumption is 4.5-7 kilocalories per pound (or 10-16 kilocalorie per kilogram) for day 1 and 3-5 kilocalories per pound (or 7-11 kilocalorie per kilogram) for day 2 to 5 and any remaining days. In a variation of the embodiments set forth above, the fasting mimicking diet provides less than 40 grams of sugar for day 1 (e.g., between 1 gram and 40 grams of sugar), less than 30 grams of sugar for days 2 to 5 and any remaining days (e.g., between 1 gram and 30 grams of sugar), less than 28 grams of protein for day 1 (e.g., between 1 gram and 40 grams of protein), less than 18 grams of protein for days 2 to 5 and any remaining days (e.g., between 1 gram and 18 grams of protein), 20-100 or 20-30 grams of monounsaturated fats or more to reach a higher calorie consumption (i.e., to reach a higher predetermined calorie consumption) for day 1, 6-30 or 6-10 grams of polyunsaturated fats or more to reach a higher calorie consumption for day 1, 2-12 grams of saturated fats or more to reach a higher calorie consumption for day 1, 10-50 or 10-15 grams of monounsaturated fats or more to reach a higher calorie consumption for days 2 to 5 and any remaining days of the fasting mimicking diet, 3-15 or 3-5 grams of polyunsaturated fats or more to reach a higher calorie consumption for days 2 to 5 and any remaining days, 1-12 or 1-6 grams of saturated fats or more to reach a higher calorie consumption for days 2 to 5, or any remaining days, and a micronutrient composition on each day and any remaining days. Details of the micronutrient composition are set forth below. To reach the higher calorie consumption described earlier which can be as high as a normal calorie intake, equal parts of the fats described above and of vegetable derived carbohydrate sources (vegetable soups and chips) described elsewhere in the patent can be used. An FMD with calories ranging from 50% restricted to normal, is expected to be effective but less effective than the 50% or more restricted diet described in this application.

In a variation, the fasting mimicking diet provides less than, in increasing order of preference, 40 grams, 30 grams, 20 grams, and 15 grams of sugar for day 1 and greater than, in increasing order of preference 10 grams, 5 grams, 1 grams, and 0 grams of sugar for day 1. In a refinement, the fasting mimicking diet provides less than, in increasing order of preference, 30 grams, 25 of sugar, 20 grams, or 15 grams of sugar for days 2 to 5 and any remaining days and greater than, in increasing order of preference, 10 grams, 5 grams, 3 grams, or 0 grams of sugar for days 2 to 5 and any remaining days.

In a further refinement, the fasting mimicking diet provides less than, in increasing order of preference, 28 grams, 25 grams, 20 grams, or 15 grams of protein for day 1 and greater than, in increasing order of preference 10 grams, 5 grams, 3 grams, or 0 grams of protein for day 1. In still a further refinement, the fasting mimicking diet provides less than, in increasing order of preference, 18 grams, 15 grams 12 grams, or 10 grams of protein for days 2 to 5 and any remaining days and greater than, in increasing order of preference, 8 grams, 5 grams 2 grams, or 0 grams of protein for days 2 to 5 and any remaining days. The amounts of monounsaturated fats, polyunsaturated fats, or monounsaturated fats can be the same as set forth above for each day of the diet. Details of the micronutrient composition are set forth above.

In another variation of the embodiments set forth above, the fasting mimicking diet provides 8-10 kcal per kilogram body weight for each diet day. In this variation, the fasting mimicking diet provides less than 30 grams of sugar for each diet day (e.g., between 1 gram and 30 grams of sugar), less than 18 grams of protein for each diet day (e.g., between 1 gram and 18 grams of protein, 9-15 grams of monounsaturated fats for each diet day, and 2.5-4.5 grams of polyunsaturated fats for each diet day and 1-5.5 grams of saturated fats for each diet day.

In still another variation of the embodiments set forth above, the fasting mimicking diet provides 5-8 kcal per kilogram body weight for each diet day. In this variation, the fasting mimicking diet provides less than 20 grams of sugar for each diet day, less than 12 grams of protein for each diet day, and 6.5-10 grams of monounsaturated fats for each diet day, 2.5-4.5 grams of polyunsaturated fats for each diet day and 1.5-4 grams of saturated fats for each diet day.

In still another variation of the embodiments set forth above, the fasting mimicking diet provides 0-3 kcal per kilogram body weight for each diet day. In this variation, the fasting mimicking diet provides less than 5 grams of sugar for each diet day, less than 3 grams of protein for each diet day, and less than 2.5 grams of monounsaturated fats for each diet day, less than 1 grams of polyunsaturated fats for each diet day and less than 1 grams of saturated fats for each diet day.

The fast mimicking diet can include virtually any source of fat, but sources high in unsaturated fat, including monounsaturated and polyunsaturated fat sources, are particularly useful. Suitable examples of monounsaturated food sources include, but are not limited to, peanut butter, olives, nuts (e.g., almonds, pecans, walnut, pistachios, cashews, macadamia), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first diet also includes a component selected from the group consisting of vegetable extracts, minerals, omega-3/6 essential fatty acids, and combinations thereof. In one refinement, such a vegetable extract provides the equivalent of 5 recommended daily servings of vegetables. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish such as salmon, tuna, mackerel, bluefish, swordfish, and the like.

In a variation, the fasting mimicking diet includes the following micronutrients (at least 95% non-animal based): over 5,000 IU of vitamin A per day (day 1 to the final day); 60-240 mg of vitamin C per day (day 1 to the final day); 400-800 mg of Calcium per day (day 1 to the final day); 7.2-14.4 mg of Iron per day (day 1 to the final day); 200-400 mg of Magnesium per day (day 1 to the final day); 1-2 mg of copper per day (day 1 to the final day); 1-2 mg of Manganese per day (day 1 to the final day); 3.5-7 mcg of Selenium per day (day 1 to the final day); 2-4 mg of Vitamin B1 per day (day 1 to the final day); 2-4 mg of Vitamin B2 per day (day 1 to the final day); 20-30 mg of Vitamin B3 per day (day 1 to the final day); 1-1.5 mg of Vitamin B5 per day (day 1 to the final day); 2-4 mg of Vitamin B6 per day (day 1 to the final day); 240-480 mcg of Vitamin B9 per day (day 1 to the final day); 600-1000 IU of Vitamin D per day (day 1 to the final day); 14-30 mg of Vitamin E per day (day 1 to the final day); over 80 mcg of Vitamin K per day (day 1 to the final day); 16-25 mcg Vitamin B12 are provided during the entire 5-day period; 600 mg of Docosahexaenoic acid (DHA, algae-derived) are provided during the entire 5-day period. The FMED diet provides high micronutrient content mostly (i.e., greater than 50 percent by weight) from natural sources including: Kale, Cashews, Yellow Bell Pepper, Onion, Lemon Juice, Yeast, and Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Collard, Tomato, Oregano, Tomato Juice, Orange Juice, Celery, Romaine Lettuce, Spinach, Cumin, Orange Rind, Citric Acid, Nutmeg, Cloves, and combinations thereof. In a refinement, the FMD provides micronutrients at greater than 25% of the recommended Daily Value (DV). These micronutrients can be provided in the micronutrient composition set forth above.

In some variations, a second diet is administered to the subject for a second time period. The second diet provides an overall calorie consumption that is within 10 percent of a subject's normal calorie consumption. Although the present invention is not significantly limited by the second time period, the second time period can be from 7 days to 6 months or longer. Typically, the second diet can be administered for 25 to 26 days or longer following the fasting mimicking and enhancing diet. In some refinements, the second diet provides at most, in increasing order of preference, 2500 kcal/day, 2400 kcal/day, 2300 kcal/day, 2200 kcal/day, 2100 kcal/day, 2000 kcal/day, 1900 kcal/day, 1800 kcal/day, 1700 kcal/day, 1600 kcal/day, or 1500 kcal/day. In some further refinements, the second diet provides at least, in increasing order of preference, 1200 kcal/day, 1300 kcal/day, 1400 kcal/day, 1500 kcal/day, 1600 kcal/day, 1700 kcal/day, or 1800 kcal/day.

In another embodiment, a diet package for administering the FMD set forth above is provided. Typically, the diet package will provide rations for each day (e.g., days 1 to 20) of the FMD as set forth above. Therefore, the step of administering the FMD can include administering the diet package. In a variation, the diet includes the caloric, food and nutritional specification set forth above in accordance to the methods and administration schedule set forth above. For example, the diet package includes a first set of rations for a first diet to be administered for a predetermined time period to a subject with administration schedule. The first diet providing less than 40 grams of sugar for day 1; less than 30 grams of sugar for days 2 to 5 and any remaining days; less than 28 grams of protein for day 1; less than 18 grams of protein for days 2 to 5 and any remaining days; 20-100 or 20-30 grams of monounsaturated fats or more to reach the higher calorie intake for day 1; 6-30 or 6-10 grams of polyunsaturated fats or more to reach the higher calorie intake for day 1; 2-12 grams of saturated fats or more to reach the higher calorie intake for day 1; 10-50 or 10-15 grams of monounsaturated fats or more to reach the higher calorie intake for days 2 to 5 and any remaining days; 3-15 or 3-5 grams of polyunsaturated fats or more to reach the higher calorie intake for days 2 to 5 and any remaining days; 1-30 or 1-6 grams of saturated fats or more to reach the higher calorie intake for days 2 to 5, or any remaining days; and a micronutrient composition on each day and any remaining days. In a refinement, the diet package also includes instructions for administering the fasting mimicking diet in accordance to the methods herein, and in particular, instructions for administering the diet package to a subject for promoting pancreatic (3-cell regeneration and somatic cell reprogramming with the instructions including the administration schedule. To reach the higher calorie consumption described earlier which can be as high as a normal calorie intake, equal parts of the fats described above and of vegetable derived carbohydrate sources (vegetable soups and chips) described elsewhere in the patent can be used. An FMD with calories ranging from 50% restricted to normal, is expected to be effective but less effective than the 50% or more restricted diet described in this application.

In a variation, the fasting mimicking diet of the diet package provides 8-25 or 8-10 kcal per kilogram body weight for each diet day; less than 30 grams of sugar for each diet day; less than 18 grams of protein for each diet day; and 9-30 or 9-15 grams of monounsaturated fats for each diet day, 2.5-9 or 2.5-4.5 grams of polyunsaturated fats for each diet day and 1-10 or 1-5.5 grams of saturated fats for each diet day. In another variation, the fasting mimicking diet of the diet package provides 5-8 kcal per kilogram body weight for each diet day; less than 20 grams of sugar for each diet day; less than 12 grams of protein for each diet day; and 6.5-10 grams of monounsaturated fats for each diet day, 2.5-4.5 grams of polyunsaturated fats for each diet day and 1.5-4 grams of saturated fats for each diet day. In still another variation, the diet package provides 0-3 kcal per kilogram body weight for each diet day; less than 5 grams of sugar for each diet day; less than 3 grams of protein for each diet day; and less than 2.5 grams of monounsaturated fats for each diet day, less than 1 grams of polyunsaturated fats for each diet day and less than 1 grams of saturated fats for each diet day.

The first set of rations can also provide 400-800 mg of calcium per day for days 1-5; 7.2-14.4 mg of iron per day for days 1-5; 200-400 mg of magnesium per day for days 1-5; 1-2 mg of copper per day for days 1-5; 1-2 mg of manganese per day for days 1-5; and 3.5-7 mcg of selenium per day for days 1-5. In a refinement, the first set of rations provides 2-4 mg of Vitamin B1 per day for days 1-5; 2-4 mg of Vitamin B2 per day for days 1-5; 20-30 mg of Vitamin B3 per day for days 1-5; 1-1.5 mg of Vitamin B5 per day for days 1-5; 2-4 mg of Vitamin B6 per day for days 1-5; 240-480 mcg of Vitamin B9 per day for days 1-5; 600-1000 IU of Vitamin D per day for days 1-5; 14-30 mg of Vitamin E per day for days 1-5; over 80 mcg of Vitamin K per day for days 1-5; and 16-25 mcg Vitamin B12 are provided during the predetermined time period. In a further refinement, the first set of rations provides 600 mg of Docosahexaenoic acid (DHA, algae-derived) during the predetermined time period. In a refinement the first set of rations also provides a component having Vitamin A in an amount of 900-1600 IU; Ascorbic Acid in an amount of 10-20 mg; calcium carbonate in an amount of 60-100 mg; ferrous fumarate in an amount of 3-6 mg; cholecalciferol in an amount of 0.001-0.005 mg; dl-alpha tocopheryl acetate in an amount 3-7 mg; phytonadione in an amount of 0.1-0.04 mg; thiamine mononitrate in an amount of 0.15-0.5 mg; riboflavin in an amount 0.2-0.6 mg; and niacinamide in an amount of 3-7 mg. In a refinement the first set of rations also provides a component having calcium pantothenate in an amount of 1.5-4.0 mg; pyridoxine hydrochloride in an amount of 0.3-0.7 mg; biotin in an amount of 0.01-0.02 mg; folic acid in an amount of 0.07-0.14 mg; cyanocobalamin in an amount of 0.001-0.002 mg; chromium picolinate in an amount of 0.014-0.022 mg; cupric sulfate in an amount of 0.18-0.32 mg; potassium iodide in an amount of 0.03-0.045 mg; magnesium oxide in an amount of 20-32 mg; manganese sulfate of 0.3-0.7 mg; sodium molybdate in an amount of 0.014-0.023 mg; sodium selenate in an amount of 0.014-0.023 mg; and zinc oxide in an amount of 3-5 mg.

In another embodiment, a method of treating neuroinflammation is provided. The method includes a step of identify a subject having neuroinflammation. A fasting mimicking diet is administered to the subject for a first time period. Typically, the step of administering the fasting mimicking diet is repeated a plurality of times at predetermined intervals. In a variation, the step of administering the fasting mimicking diet can be accomplished with the diet package as set forth above. Details of the fasting mimicking diet, repetition of the fasting mimicking diet, second diet, and scheduling of the fasting mimicking diet (e.g., first time period, second time period, etc.) and the second diet are the same as set forth above.

In another embodiment, a method of treating Mild Cognitive Impairment (MCI) is provided. The method includes a step of identifying a subject having MCI, and in particular, amnestic MCI. A fasting-mimicking diet is administered to the subject for a first time period as set forth above. Subjects with amnestic MCI, and in particular amnestic MCI, have more memory issues than normal for subjects of the same age. However, symptoms of subjects with MCI (and in particular amnestic MCI) are not as severe as those of people with Alzheimer's disease. MCI can be diagnosed by thinking, memory, and language tests. Typically, the step of administering the fasting-mimicking diet is repeated a plurality of times at predetermined intervals. Details of the fasting mimicking diet, repetition of the fasting mimicking diet, second diet, and scheduling (e.g., first time period, second time period, etc.) of the fasting mimicking diet and the second diet are the same as set forth above.

The following examples illustrate the various embodiments of the present invention. Those skilled in the art will recognize many variations that are within the spirit of the present invention and scope of the claims.

The experimental mouse FMD is based on a nutritional screen that identifies ingredients which allow high nourishment during periods of low calorie consumption[5]. The FMD diet consists of two different components designated as day 1 diet and day 2-4 (males) or 2-5 (females) diet that were fed in this order respectively. Day 1 diet contains 2.47 kcal/g, the day 2-4 or 2-5 diet is identical on all feeding days and contains 1.63 kcal/g. Day 1 and day 2-4/5 diets were supplied to the FMD cohort with the average intake of the ad lib control group (~4 g) every two weeks. The 4% PR diet is a low, casein-based protein diet containing 3.87 kcal/g, fed for 7 consecutive days to male and female mice in the 4% PR cohort. Mice consumed all the supplied food on each day of the FMD and 4% PR regimens and showed no signs of food aversion. Prior to supplying the diets, animals were transferred into fresh cages to avoid feeding on residual chow and coprophagy. The experiments utilized another AD mouse model, the E4FAD-Tg mouse model, developed by the LaDu lab[6]. Designed to mimic the late-onset form of the disease and regulated by apolipoprotein expression (APOE), this model has been generated by crossing 5×FAD mice (expressing five FAD-associated mutations) with mice expressing the human apoE 4 isoforms[6]. Those carrying the APOE4 allele are at greatest risk of developing AD compared to those with the APOE3 or APOE2 alleles[7].

The administration of the FMD began at early age (3.5 months) and concluded at old age (~18.5 months) in male and female 3×Tg-AD mice. The administration of the FMD began at early age (3 months) and concluded at mid-age (~7 months), when AB pathology extensively impacted the hippocampal and cortex regions of female E4FAD mice. Data collected to-date that these dietary regimens reduce the levels of AD-associated pathology, improve cognitive behavior, reduce neuroinflammation and increase levels of hippocampal neurogenesis.

The experiments show that FMD formulations can reduce AD-associated pathology, improve cognitive performance, and increase hippocampal neurogenesis when administered to the 3×Tg-AD model at an earlier age and for a longer duration (FIG. 2-5). Moreover, FIG. 6 shows that FMD formulations can reduce AD-associated pathology in the E4FAD-Tg mouse model after ~4 months of bi-weekly FMD cycles. FIG. 7 shows that weekly FMD cycles mediate microglia number, and in turn, reduce neuroinflammation in aged 3×Tg mice.

Figures 1A, 1B, 1C:
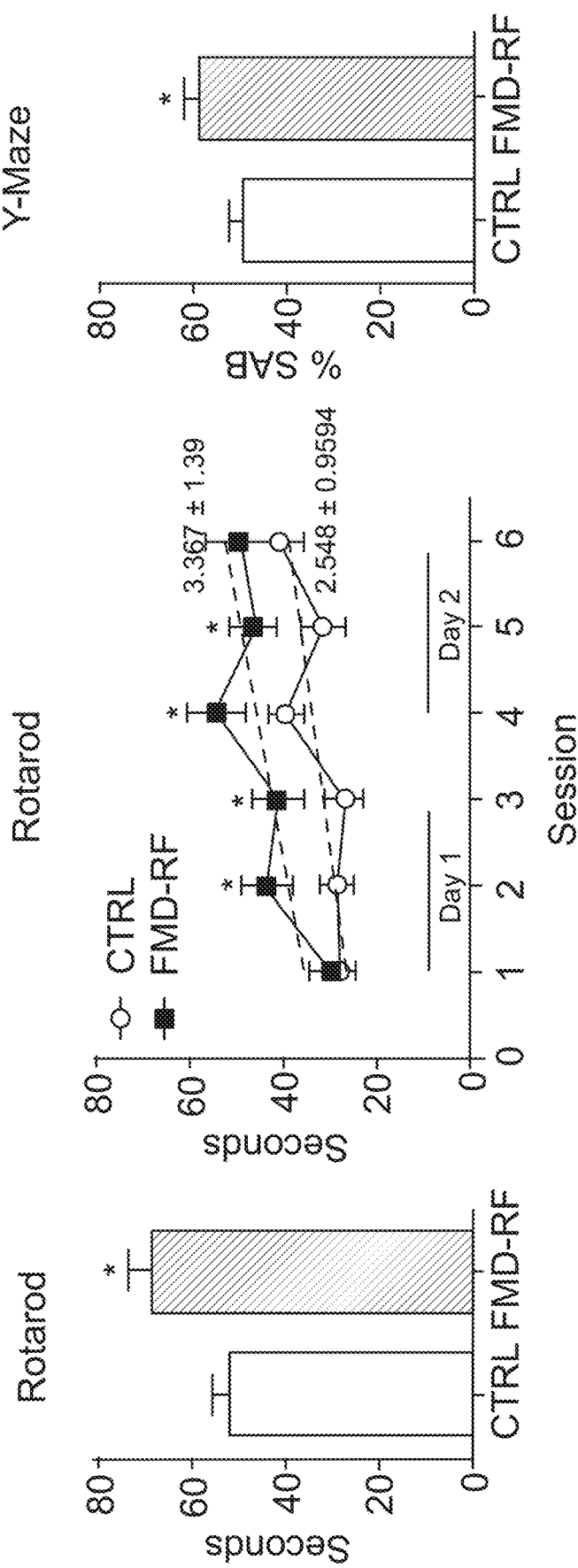
FIGS. 1A, 1B, 1C, 1D, 1E, 1F, 1G, 1H, 1I, 1J, and 1K: Periodic FMD cycle improves motor coordination, hippocampal-dependent learning, and short- and long-term memory in aged wild-type mice. The graphs were adapted from Brandhorst et al.[3] (A) Best rotarod performance score at 23 months. n=18/group. (B) Rotarod performance as linear regression for each cohort (dashed lines). n=18/group. (C) Spontaneous alternation behavior (SAB) at 23 months. n=11/group. (D) Recognition index at 23 months in the novel object recognition task. (E) Exploration time of the old versus novel object (New, dashed bar). n=8/group. (F-I) Error number (F), deviation (G), latency (H), and success rate (I) in the Barnes maze at 23 months. n=7-12/group. (J and K) Control (J) and FMD-RF (K) strategies used to locate escape box. All data are expressed as the mean±SEM.
Figures 1D, 1E:
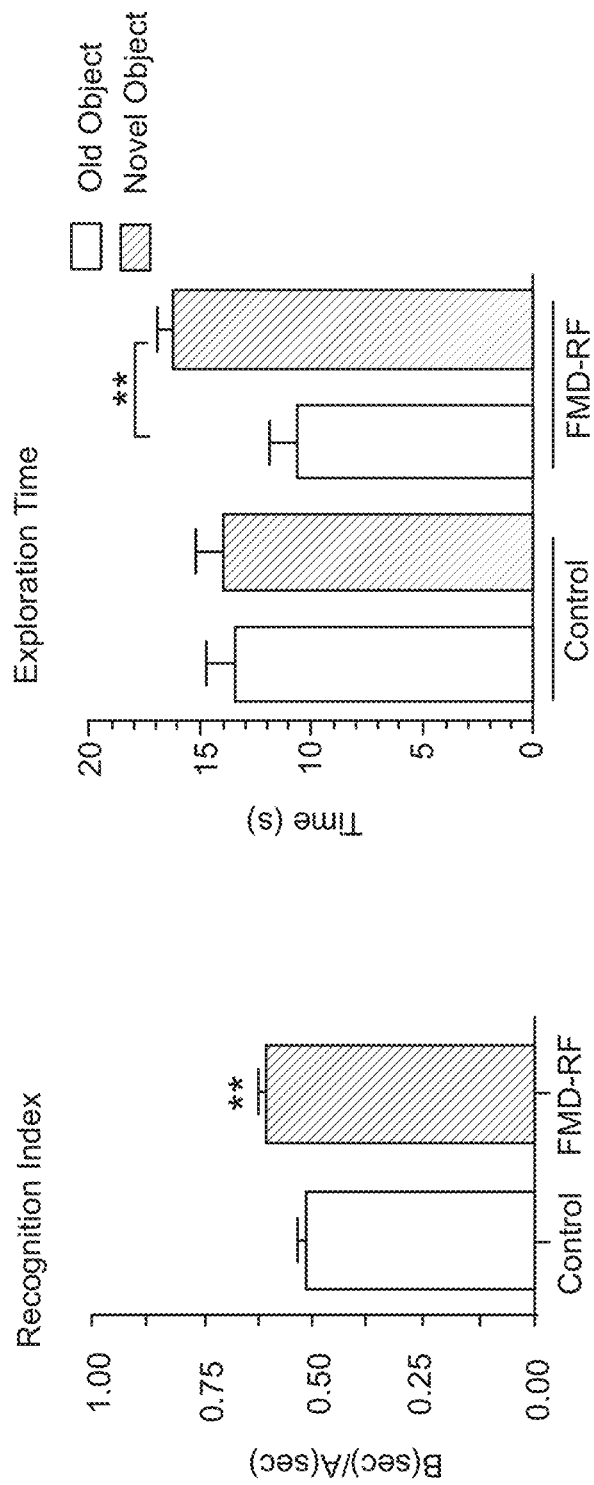
Figure 1G:
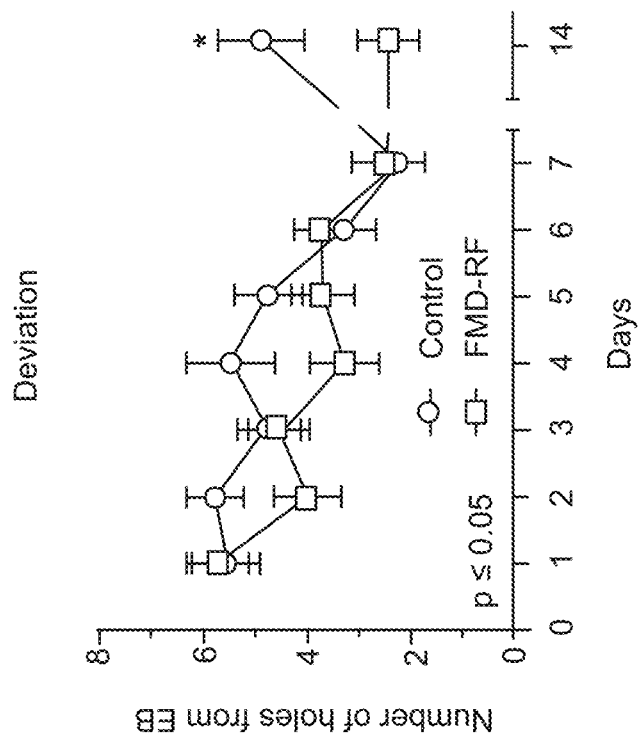
Figure 1F:
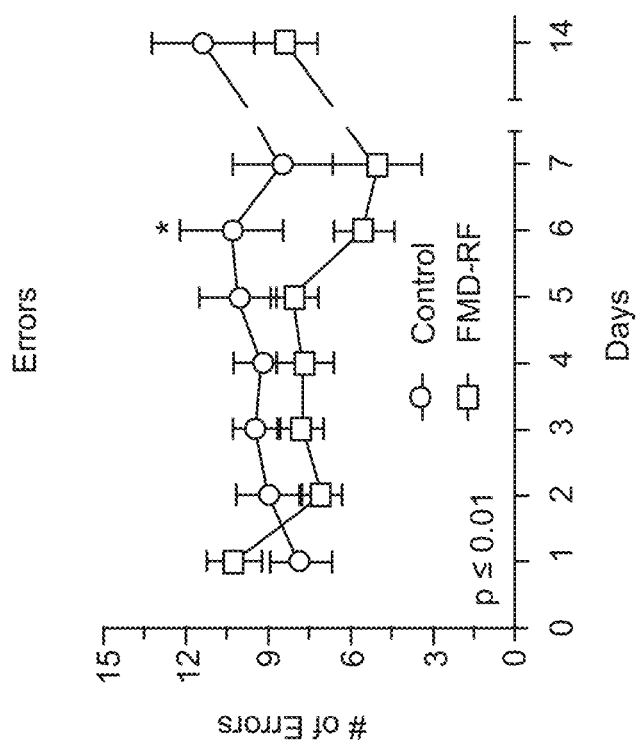
Figure 1I:
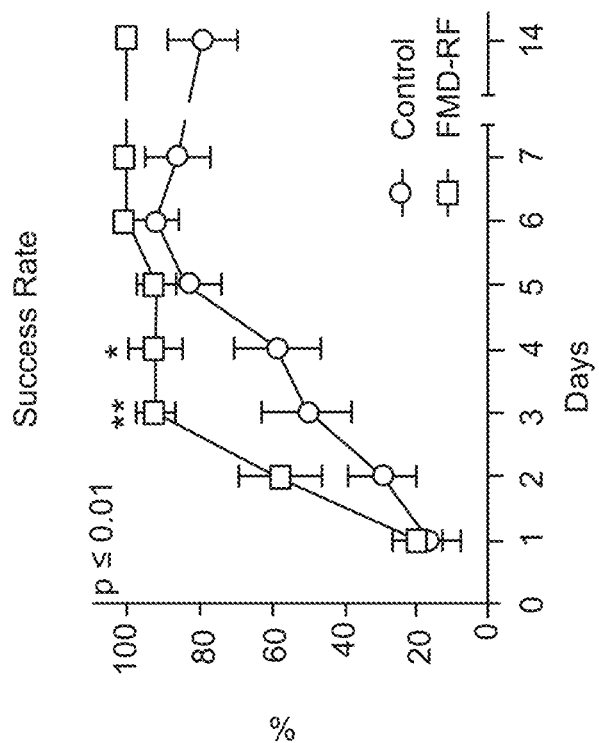
Figure 1H:
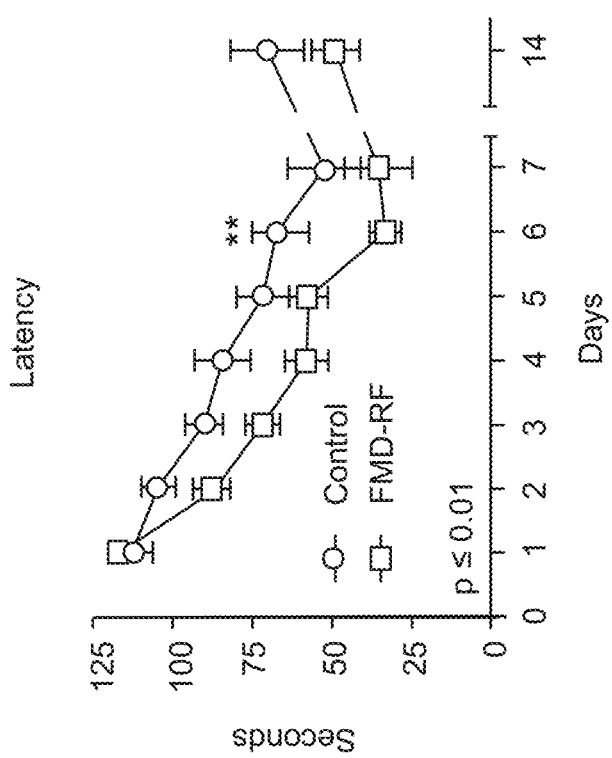
Figures 1J, 1K:
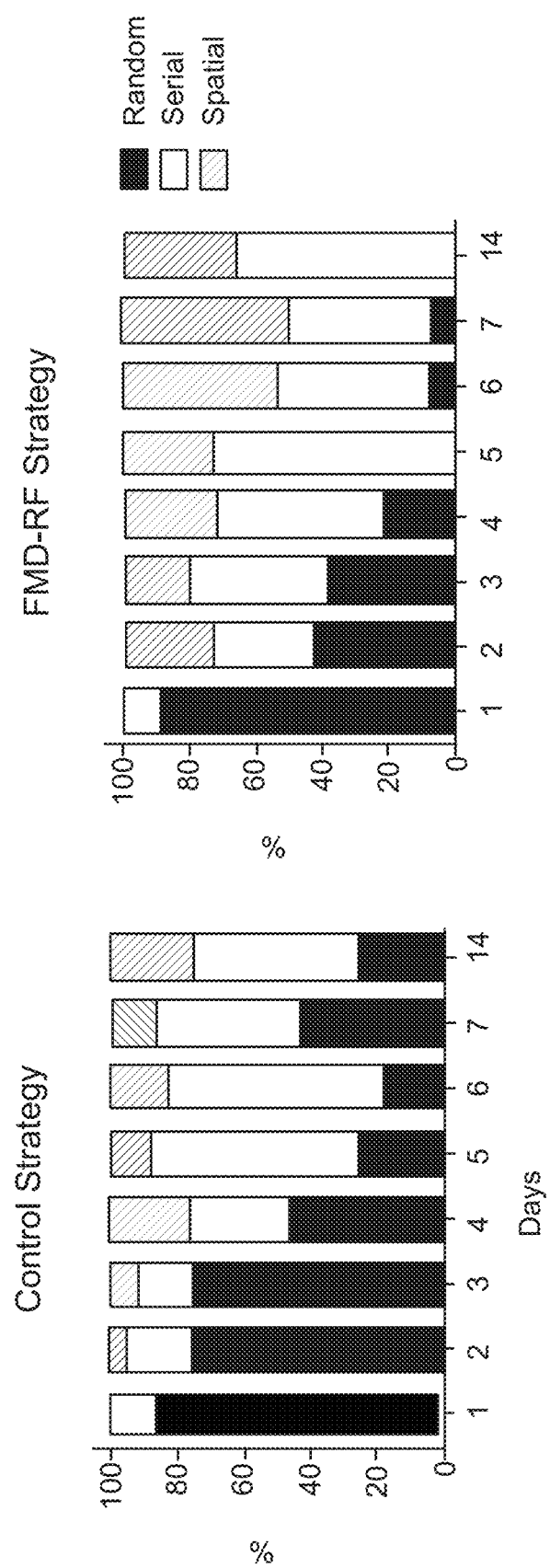

FIGS. 1A-1K demonstrate that periodic FMD cycle improves motor coordination, hippocampal-dependent learning, and short- and long-term memory in aged wildtype mice. The graphs were adapted from Brandhorst et al.[3] FIG. 1A shows the best rotarod performance score at 23 months (n=18/group). The rotarod performance test is a performance test for the mice in which a rotating rod has forced motor activity applied there to by the mice. FIG. 1B provides rotarod performance as linear regression for each cohort (dashed lines). (n=18/group). The Y-Maze tests is used to assess short-term working memory, with unique alternations in the maze incorporated into a spontaneous alternation behavior (SAB) score. Mice with a high SAB scores tend to exhibit improved short-term working memory. FIG. 1C provides SAB at 23 months (n=11/group). The novel object recognition (NOR) test is used to assess short-term spatial memory. FIG. 1D provides the recognition index at 23 months in the novel object recognition task. FIG. 1E provides the exploration time of the old versus novel object (New, dashed bar). (n=8/group). The Barnes maze behavior test is used to assess long-term spatial memory. FIGS. 1F-I provide the Error number (F), deviation (G), latency (H), and success rate (I) in the Barnes maze at 23 months. (n=7-12/group). FIG. 1J provides control strategies and FIG. 1K provides FMD-RF strategies used to locate escape box.

Figure 2A:
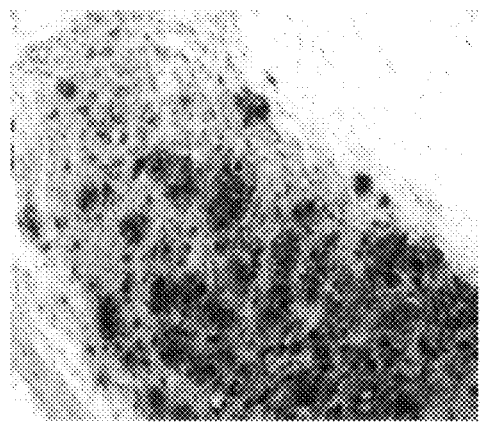
FIGS. 2A, and 2B. Bi-weekly FMD cycles administered for 15 months in female 3×Tg-AD mice reduces levels of AD-associated pathology at 18.5 months of age. (A) Subiculum amyloid load in 18.5 month old female 3×Tg-AD mice on control (left) or FMD (right) diet. (B) Quantitative measurements of amyloid load (%).
Figure 2A:
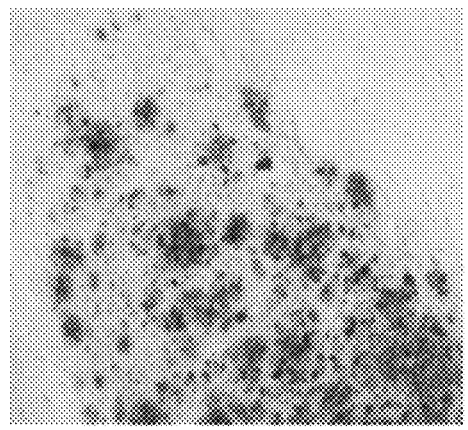
Figure 2B:
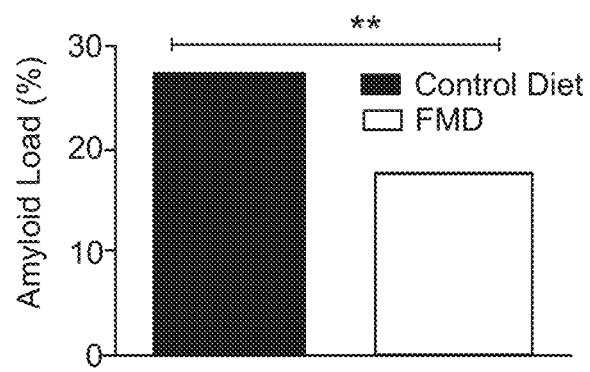

FIGS. 2A and 2B shows that bi-weekly FMD cycles administered for 15 months in female 3×Tg-AD mice reduces levels of AD-associated pathology at 18.5 months of age. FIG. 2A provides subiculum amyloid load in 18.5 month old female 3×Tg-AD mice on control (left) or FMD (right) diet. FIG. 2B provides quantitative measurements of subiculum amyloid load (%).

Figure 3A:
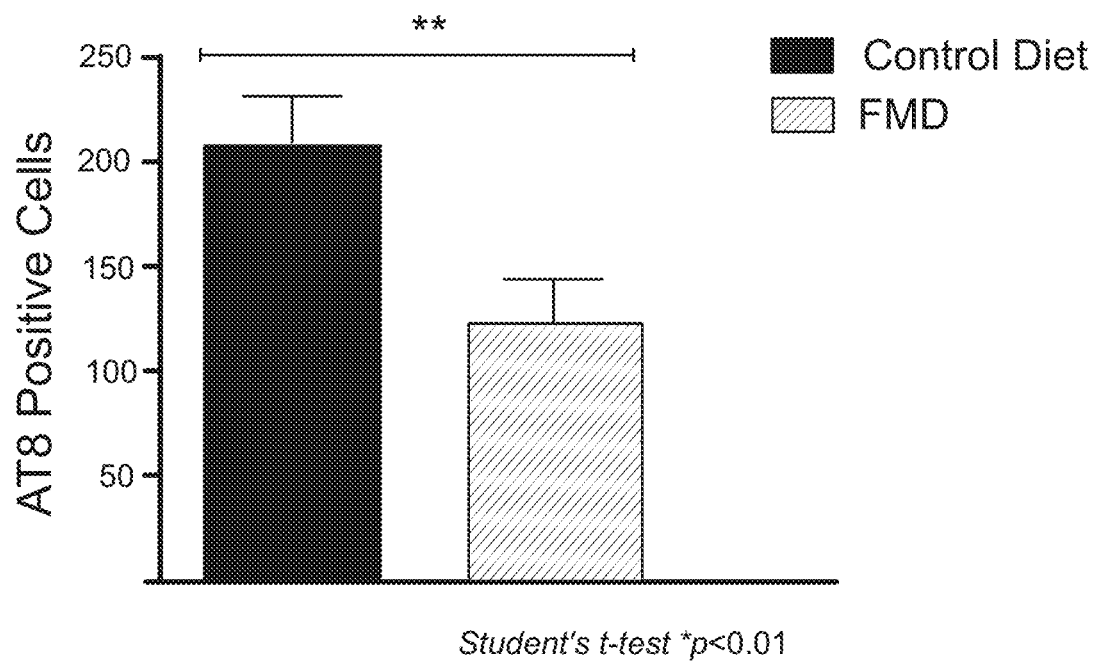
FIGS. 3A, 3B-1, and 3B-2. Bi-weekly FMD cycles administered for 15 months in male 3×Tg-AD mice reduces levels of AD-associated pathology at 18.5 months of age. (A) Quantitative measurements of total hyperphosphorylated tau count in the hippocampus of 18.5 month old male 3×Tg-AD mice in control and FMD cohorts. (B) IHC-based visualization of hyperphosphorylated tau count in the hippocampus of 18.5 month old male 3×Tg-AD mice in control and FMD diet cohorts.
Figures 1, 3B:
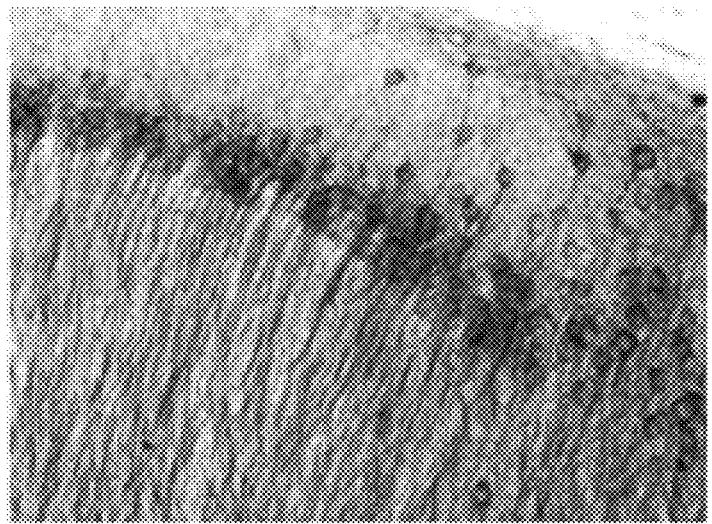
Figures 2, 3B:
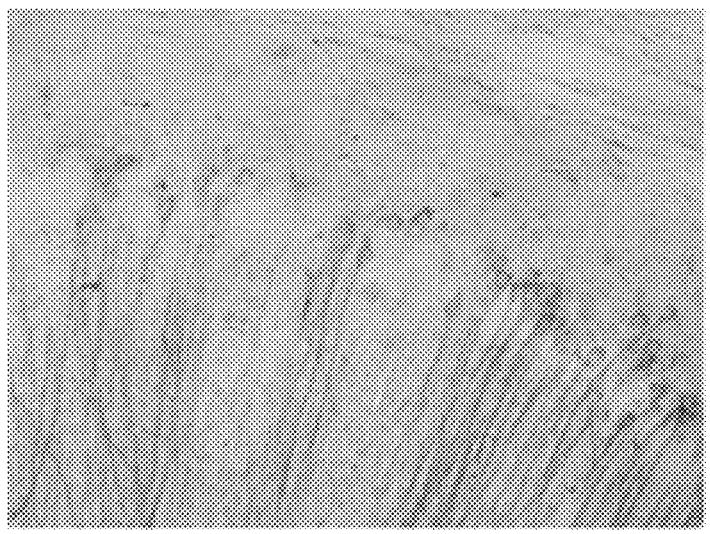

FIGS. 3A-3B demonstrates that bi-weekly FMD cycles administered for 15 months in male 3×Tg-AD mice reduces levels of AD-associated pathology at 18.5 months of age. FIG. 3A provides quantitative measurements of total hyperphosphorylated tau count in the hippocampus of 18.5 month old male 3×Tg-AD mice in control diet and FMD cohorts. (B) IHC-based visualization of hyperphl2osphorylated tau count in the hippocampus of 18.5 month old male 3×Tg-AD mice in control diet and FMD cohorts.

Figure 4A:
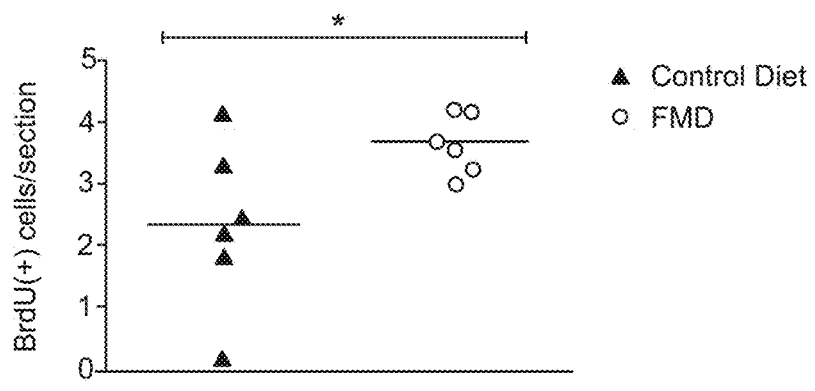
FIGS. 4A and 4B: Bi-weekly FMD cycles administered for 15 months in female 3×Tg-AD mice promotes neurogenesis as seen by increased cell proliferation in the hippocampus. (A) Quantitative measurements of BrdU+ cells/ hippocampal section for control and FMD diet cohorts. (B) IHC-based visualization of BrdU⁺ cells in the hippocampus of a 1 month old wild-type mouse pup (positive control), 18.5 month old female 3×Tg-AD mice of control diet (middle) and FMD (right) cohort.
Figure 4B:
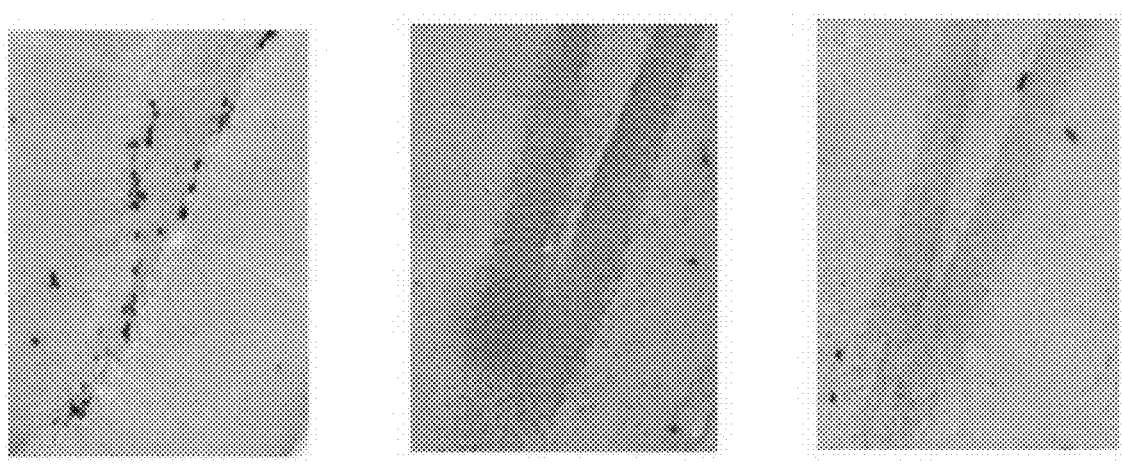

FIGS. 4A-4B demonstrate that bi-weekly FMD cycles administered for 15 months in female 3×Tg-AD mice promotes neurogenesis as seen by increased cell proliferation in the hippocampus. (A) Quantitative measurements of BrdU+ cells/hippocampal section for control diet and FMD cohorts. (B) IHC-based visualization of BrdU+ cells in the hippocampus of a 1 month old wild-type mouse pup (positive control), 18.5 month old female 3×Tg-AD mice of control (middle) and FMD (right) cohorts.

FIG. 5 demonstrate thats bi-weekly FMD cycles improve hippocampal-dependent working short-term memory in 3×Tg-AD mice. The figure shows spontaneous alternation behavior (SAB) at midpoint of study (10.5 months) for female 3×Tg-AD mice. n=9-14/group.

FIGS. 6A and 6B demonstrate that FMD cycles reduce Aβ plaques and triton-soluble, oligomeric Aβ in E4FAD female mice (AD mouse model expressing mutations in APP and knock-in of the human apoE4 allele developed by Youmans et al.)[5]. (A) DAB-immunohistochemistry of Aβ plaques in subiculum of 7.5-month-old E4FAD female mice on control diet or after ~4 months of bi-weekly FMD cycles. (B) Subiculum Aβ load (%) in cortex of 7.5-month-old E4FAD female mice on control diet or after ~4 months of bi-weekly FMD cycles. (n=18/group).

FIGS. 7A-7B demonstrate that bi-weekly FMD cycles reduce neuroinflammation by mediating microglia number in aged 3×Tg mice. FIG. 7A provides representative images showing CD11b-ir microglia in hippocampus sections of 18.5-month-old female C57B/6 wildtype, 3×Tg Control and 3×Tg FMD mice (top). FIG. 7 shows quantification of total numbers of CD11b-ir cells in hippocampus CA1 and subiculum combined brain regions of C57B/6 wildtype, 3×Tg Control, and 3×Tg FMD groups (bottom left; n=5-7 animals/group).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Bloom, G. S. (2014, April). Amyloid-β and Tau. JAMA Neurology JAMA Neurol, 71(4). 505-508.
2. Elder, G., Gama Sosa, M., & De Gasperi, R. (2010, January/February). Transgenic mouse models of Alzheimer's disease. Mt Sinai J Med., 77(1). 69-81.
3. Brandhorst, S., Choi, I., Wei, M., Cheng, C., Sedrakyan, S., Navarrete, G., . . . Longo, V. (2015, July 7). A Periodic Diet that Mimics Fasting Promotes Multi-System Regeneration, Enhanced Cognitive Performance, and Healthspan. Cell Metabolism, 22(1). 86-99.
4. Wei, M., Brandhorst, S., Shelehchi, M., Mirzaei, H., Cheng, C W, Budniak, J., Groshen, S., Mack, W J, E., Di Biase. S., Cohen, P., Morgan, T E, Dorff, T., Hong, K., Michalsen, A., Laviano, A., Longo, V D. (2017). Fasting-mimicking diet and markers/risk factors for aging, diabetes, cancer, and cardiovascular disease. Sci transl med. 9(377). Parrella, E., Maxim, T., Maialetti, F., Zhang, L., Wan, J., Wei, M., . . . Longo, V. D. (2013, April). Protein restriction cycles reduce IGF-1 and phosphorylated Tau, and improve behavioral performance in an Alzheimer's disease mouse model. Aging Cell, 12(2). 257-268.
5. Youmans, K. L., Tai, L. M., Nwabuisi-Heath, E., Jungbauer, L., Kanekiyo, T., Gan, M., . . . Ladu, M. J. (2012, December 7). APOE4-specific Changes in A B Accumulation in a New Transgenic Mouse Model of Alzheimer Disease. Journal of Biological Chemistry, 287 (50). 41774-41786.
6. Liu, C., Kanekiyo, T., Xu, H., & Bu, G. (2013, February). Apolipoprotein E and Alzheimer disease: Risk, mechanisms and therapy. Nature Reviews Neurology Nat Rev Neurol, 9(2). 106-118.

PUBLICATIONS

1. P. Rangan, F. Lobo, G. Navarrete, M. Wei, V. D. Longo. The effects of a protein-restricted dietary intervention on a triple transgenic mouse model of Alzheimer's disease. Cell Symposia: Neuro-Immune Axis: Reciprocal Regulation in Development, Health, and Disease, Sitges, Spain, Sep. 17-19, 2017.
2. TITLE Manuscript Number: THELANCETNEUROLOGY-D-16-00304
3. Choi I Y, Piccio L, Childress P, Bollman B, Ghosh A, Brandhorst S, Suarez J, Michalsen A, Cross A H, Morgan T E, Wei M, Paul F, Bock M, Longo V D. A Diet Mimicking Fasting Promotes Regeneration and Reduces Autoimmunity and Multiple Sclerosis Symptoms. Cell reports. 2016; 15(10):2136-46. doi: 10.1016/j.celrep.2016.05.009. PubMed PMID: 27239035; PMCID: PMC4899145.
4. Brandhorst S, Choi I Y, Wei M, Cheng C W, Sedrakyan S, Navarrete G, Dubeau L, Yap L P, Park R, Vinciguerra M, Di Biase S, Mirzaei H, Mirisola M G, Childress P, Ji L, Groshen S, Penna F, Odetti P, Perin L, Conti P S, Ikeno Y, Kennedy B K, Cohen P, Morgan T E, Dorff T B, Longo V D. A Periodic Diet that Mimics Fasting Promotes Multi-System Regeneration, Enhanced Cognitive Performance, and Healthspan. Cell Metab. 2015; 22(1):86-99. doi: 10.1016/j.cmet.2015.05.012. PubMed PMID: 26094889; PMCID: PMC4509734.
5. Levine M E, Suarez J A, Brandhorst S, Balasubramanian P, Cheng C W, Madia F, Fontana L, Mirisola M G, Guevara-Aguirre J, Wan J, Passarino G, Kennedy B K, Wei M, Cohen P, Crimmins E M, Longo V D. Low protein intake is associated with a major reduction in IGF-1, cancer, and overall mortality in the 65 and younger but not older population. Cell Metab. 2014; 19(3):407-17. doi: 10.1016/j.cmet.2014.02.006. PubMed PMID: 24606898; PMCID: PMC3988204.
6. Longo V D, Mattson M P. Fasting: molecular mechanisms and clinical applications. Cell Metab. 2014; 19(2):181-92. doi: 10.1016/j.cmet.2013.12.008. PubMed PMID: 24440038; PMCID: 3946160.
7. Parrella E, Maxim T, Maialetti F, Zhang L, Wan J, Wei M, Cohen P, Fontana L, Longo V D. Protein restriction cycles reduce IGF-1 and phosphorylated Tau, and improve behavioral performance in an Alzheimer's disease mouse model. Aging Cell. 2013; 12(2):257-68. doi: 10.1111/acel.12049. PubMed PMID: 23362919; PMCID: 3982836.
8. Parrella E, Longo V D. Insulin/IGF-I and related signaling pathways regulate aging in nondividing cells: from yeast to the mammalian brain. ScientificWorldJournal. 2010; 10:161-77. doi: 10.1100/tsw.2010.8. PubMed PMID: 20098959.
9. Wei M, Brandhorst S, Shelehchi M, Mirzaei H, Cheng C W, Budniak J, Groshen S, Mack W J, Guen E, Di Biase S, Cohen P, Morgan T E, Dorff T, Hong K, Michalsen A, Laviano A, Longo V D. Fasting-mimicking diet and markers/risk factors for aging, diabetes, cancer, and cardiovascular disease. Sci Transl Med. 2017; 9(377). PubMed PMID: 28202779.

What is claimed is:

1. A method of treating Alzheimer's disorders associated with APOE4 apolipoprotein expression comprising:
   a) identifying a subject having an Alzheimer's disorder associated with APOE4 apolipoprotein expression; and
   b) administering a fasting mimicking diet (FMD) to the subject for a first time period, wherein the FMD provides 2.47 kcal/g plus or minus 30 percent on day 1 and 1.63 kcal/g plus or minus 30 percent on day 2, wherein the FMD is administered for only 1 day with a frequency of at least 1 day/week every week of a month or wherein the FMD will substitute a subject's normal diet for a period of 2 days every week.

2. The method of claim 1 wherein the Alzheimer's disorder associated with APOE4 apolipoprotein expression exhibits amyloid plaque formation.

3. The method of claim 1 wherein the Alzheimer's disorder associated with APOE4 apolipoprotein expression exhibits levels of tau protein in the subject.

4. The method of claim 1 wherein the fasting mimicking diet is administered for a period of 4 to 10 days every 2-12 weeks.

5. The method of claim 1 wherein step b) is repeated a plurality of times at predetermined intervals.

6. The method of claim 5 wherein step b) is repeated at intervals from one week to 6 months.

7. The method of claim 5 wherein the subject is administered a normal diet in between repetition of step b).

8. The method of claim 1 wherein the FMD provides 4.5-7 kcal per pound of body weight (or 10-16 kcal per kilogram body weight).

9. The method of claim 1 wherein on day 1, the FMD provides less than 30 grams of sugar, less than 28 grams of protein, 20-30 grams of monounsaturated fats, 6-10 grams of polyunsaturated fats and 2-12 grams of saturated fats.

10. The method of claim 9 wherein on days 2-5 the FMD provides less than 20 grams of sugar, less than 18 grams of protein, 10-15 grams of monounsaturated fats, 3-5 grams of polyunsaturated fats and 1-6 grams of saturated fats.

11. The method of claim 10 wherein the FMD also provides micronutrients at greater than 25% of the recommended Daily Value (DV).

12. The method of claim 1 wherein the FMD provides 3-5 kcal per pound of body weight.

13. The method of claim 12 wherein the day 1 FMD diet contains less than 30 grams of sugar, less than 28 grams of protein, 20-30 grams of monounsaturated fats, 6-10 grams of polyunsaturated fats and 2-12 grams of saturated fats.

14. The method of claim 13 wherein the day 2 FMD diet includes less than 20 grams of sugar, less than 18 grams of protein, 10-15 grams of monounsaturated fats, 3-5 grams of polyunsaturated fats and 1-6 grams of saturated fats.

15. The method of claim 13 wherein the step of administering the fasting mimicking diet includes administering a diet package that provides caloric, food and nutritional specification, and administration schedule of the fasting mimicking diet.

* * * * *